United States Patent [19]
Saini et al.

[11] Patent Number: 5,737,457
[45] Date of Patent: Apr. 7, 1998

[54] CHIP LEVEL WAVEGUIDE SENSOR

[75] Inventors: Devinder P. Saini; Stanley M. Klainer; Stephen L. Coulter, all of Henderson, Nev.

[73] Assignee: FCI - FiberChem, Inc., Las Vegas, Nev.

[21] Appl. No.: 587,231

[22] Filed: Jan. 16, 1996

Related U.S. Application Data

[63] Continuation of Ser. No. 511,959, Aug. 7, 1995, Pat. No. 5,650,123, which is a continuation-in-part of Ser. No. 201,796, Feb. 25, 1994, Pat. No. 5,439,647.

[51] Int. Cl.⁶ .................................................. G02B 6/00
[52] U.S. Cl. ........................................ 385/12; 250/227.18
[58] Field of Search ............................... 385/10–12, 141, 385/142, 143; 250/227.18, 227.23; 356/320, 408, 409, 410, 411, 412, 425, 434, 435

[56] References Cited

U.S. PATENT DOCUMENTS

| | | | |
|---|---|---|---|
| 5,307,146 | 4/1994 | Porter et al. | 356/320 |
| 5,340,715 | 8/1994 | Slovacek et al. | 385/12 |

*Primary Examiner*—Akm E. Ullah
*Attorney, Agent, or Firm*—Henry P. Sartorio

[57] ABSTRACT

Waveguide sensors are formed on a chip package which contains at least one source and at least one detector. Simple waveguide elements are mounted on the chip. Waveguide defining elements can also be formed integrally with the chip package so that simple waveguide bodies can be inserted or removed. Various geometries of source, reference detector, and sensing detector can be produced. A liquid waveguide sensor is formed by filling a waveguide channel with a liquid reagent or reagents homogeneously dispersed in sol-gels. Sensing waveguides are made of or contain chemistries or biochemistries or are uncoated. Reference waveguides are made of or contain chemistries, biochemistries or materials which are inert to the analyte (sample) of interest. The chip geometries are such that absorption, fluorescence, and refractive index measurements can be made.

22 Claims, 10 Drawing Sheets

CHIP LEVEL WAVEGUIDE SENSOR

RELATED APPLICATIONS

This application is a continuation of Ser. No. 08/511,959 filed Aug. 7, 1995 now U.S. Pat. No. 5,650,123, which is a continuation-in-part of Ser. No. 08/201,796 filed Feb. 25, 1994, now U.S. Pat. No. 5,439,647.

BACKGROUND OF THE INVENTION

The invention relates generally to optical sensors, and more particularly to optical waveguide chemical biochemical sensors.

A variety of optical chemical biochemical sensors based on optical fibers and other waveguides have been developed. For example, U.S. Pat. No. 4,846,548 to Klainer, U.S. Pat. No. 4,929,049 to LeGoullon et al., U.S. Pat. No. 5,026,139 to Klainer et al., U.S. Pat. No. 5,165,005 to Klainer et al., and U.S. Pat. No. 5,405,583 to Goswami et al., address solid state optical chemical and biochemical sensors. U.S. Pat. Nos. 4,892,383, 5,059,790, and 5,116,759 to Klainer et al., show reservoir type sensors. A wide variety of sensing chemistries or biochemistries are illustrated. There are also bare fiber optrodes in which a bare sensing region of the fiber is used. In virtually all designs, an external source and detector are optically coupled to the waveguide.

A problem with the prior art is that the entire sensor is not integrated, i.e., external source and detector, and the entire waveguide must be replaced for a different sensing chemistry or biochemistry. Accordingly, it would be desirable to provide a waveguide chemical or biochemical sensor with integrated structure and in which the sensing chemistry or biochemistry can be easily changed.

SUMMARY OF THE INVENTION

Accordingly, it is an object of the invention to provide waveguide chemical biochemical sensors with integrated structures.

It is also an object of the invention to provide waveguide chemical biochemical sensors with interchangeable sensing chemistries and biochemistries.

The invention is a waveguide chemical or biochemical sensor having at least one waveguide arm mounted on a substrate or chip having at least one source and at least one detector formed integrally therein. The waveguide arms can be fixedly mounted on the substrate (e.g., by gluing) or removably attached (e.g., by mechanical clips). The waveguide arms, or parts thereof, can also be formed (e.g., molded) as part of the substrate or chip itself. A reference channel can be included. Reflective end faces of the waveguide arms direct light transmitted therethrough to a detector in the substrate.

Different sensing arms can be coated with or formed of different sensing chemistries or biochemistries. The sensing arms can also be uncoated. The basic mechanism of sensing using sensing and reference arms is a comparison of the sensing and reference arms where the sensing arm is affected by the target analyte and the reference arm is not. Thus the sensing arm can be coated or uncoated, the reference arm can be coated or uncoated, but both cannot be uncoated at the same time. If there are multiple sensing and reference arms, some can be coated while others can be uncoated.

DETAILED DESCRIPTION OF THE PREFERRED EMBODIMENTS

Figure 1A:
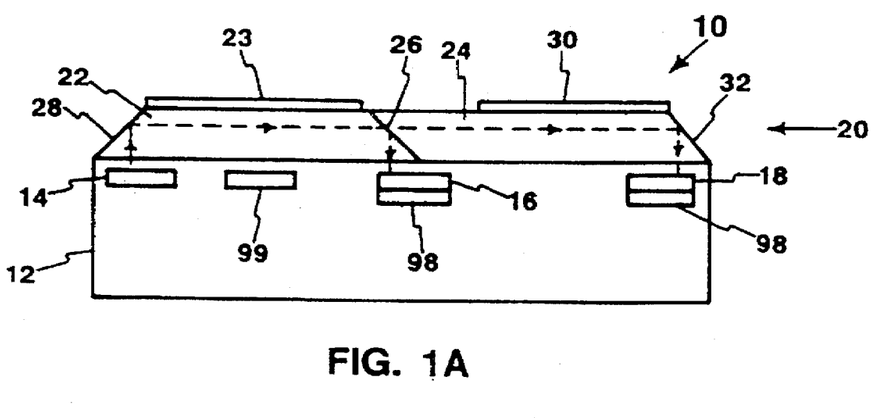
FIGS. 1A,B are side and perspective views of a waveguide sensor having a reference arm and sensing arm.
Figure 1B:
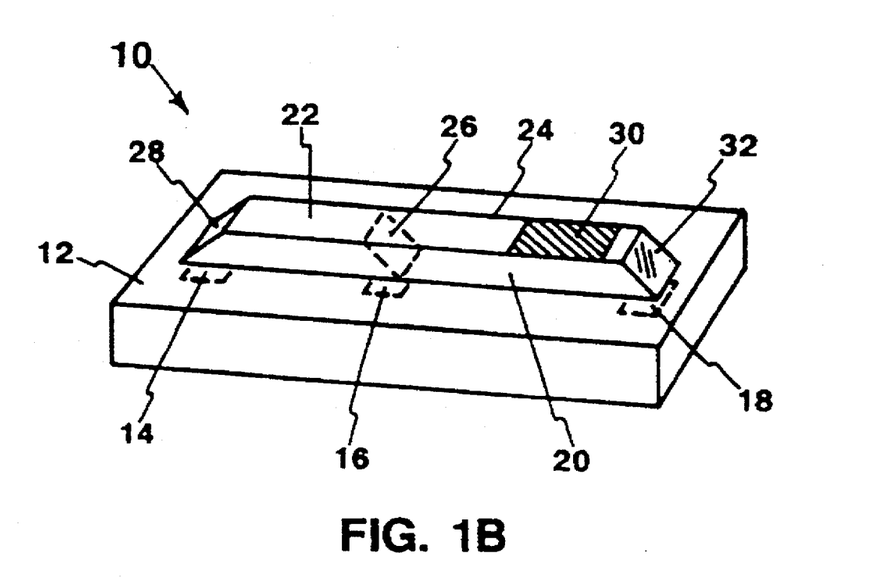

As shown in FIGS. 1A,B, a waveguide sensor 10 is formed on a substrate or chip 12 which contains a light source 14 and a pair of detectors 16,18 integrally formed therein. The source 14 and detectors 16,18 are linearly aligned, with source 14 at one end; however, different geometries can also be used. A waveguide 20 formed of a reference arm 22 and sensing arm 24 is mounted on substrate 12 in alignment with source 14 and detectors 16,18. Arms 22,24 are separated by beam splitter 26. Beam splitter 26 is formed by abutting the sloped ends of reference arm 22 and sensing arm 24, and applying suitable optical coatings to produce desired reflection and transmission. Light from source 14 under sloped reflective end face 28 is incident thereon and reflects to send a light beam down waveguide 20. Beam splitter 26 reflects a portion of the light down to the underlying reference detector 16 and transmits the remainder of the light through sensing arm 24 which has a sensing region 30 formed on a portion thereof. The light beam passing through sensing arm 24 is affected by sensing region 30 as it interacts with a sample.

Sensing region 30 may be a sensing chemistry or biochemistry coated on sensing arm 24. Various types of sensing chemistries and biochemistries can be used including, but not limited to, inorganics, organics, polymers, metals, metal compounds, organometallics, bio-inorganics, enzymes, antibodies and microbes. U.S. Pat. Nos. 4,846,548, 4,892,383, 4,929,049, 5,026,139, 5,059,790, 5,116,759, 5,165,005, 5,405,583, which describe many specific chemistries and biochemistries, are herein incorporated by reference.

Alternately, sensing region 30 may be an uncoated (bare) region on sensing arm 24 since a target analyte may change the waveguiding properties of a bare waveguide. With either a coated or uncoated waveguide, properties measured include absorption, fluorescence, and refractive index. The resulting light is incident on sloped reflective end face 32 which reflects the light downward onto detector 18. Reference arm 22 is covered by coating 23 or in some cases could be uncovered if the analyte does not affect the uncoated waveguide. Either sensing arm 24 can be uncoated or reference arm 22 can be uncoated, but not both. Permissible combinations are coated sensing arm 24 and coated reference arm 22, coated sensing arm 24 and uncoated reference arm 22 or uncoated sensing arm 24 and coated reference arm 22.

As shown in FIG. 1A, the substrate 12 is preferably a molded semiconductor chip package. Source 14 is typically an LED or laser diode. Detectors 16,18 are typically photodiodes (e.g., silicon photodiodes). The source 14 and detectors 16,18 are integrally formed in the chip package but are not on the surface thereof. The chip package is made of optically transparent material and also protects the source and detectors from the environment.

Figure 1C:
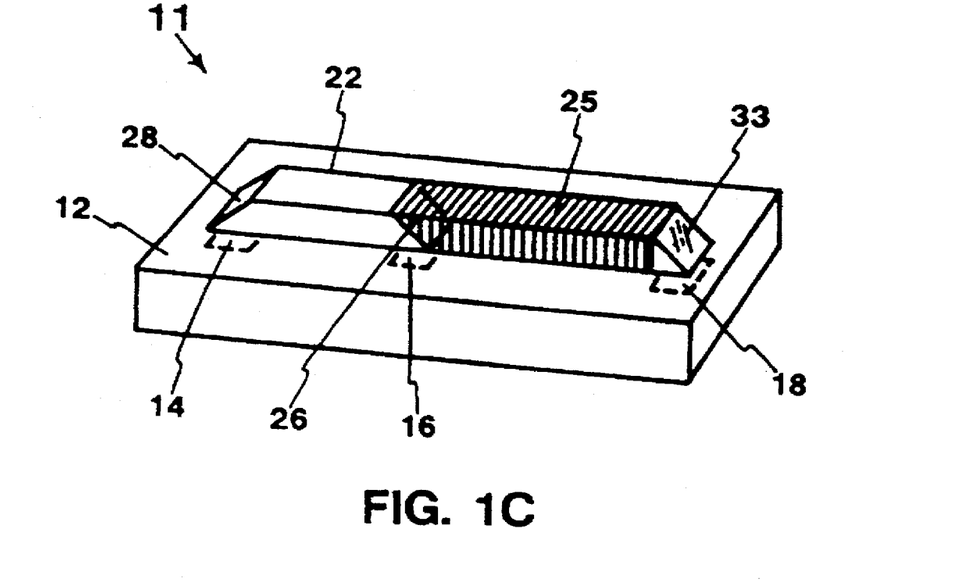
FIG. 1C is a perspective view of the waveguide sensor of FIGS. 1A,B wherein the sensing arm waveguide is formed of the sensing chemistry.

FIG. 1C shows a waveguide sensor 11 which is similar to sensor 10 of FIGS. 1A,B except that sensing arm 24 is replaced with sensing arm 25 which is formed of the sensing chemistry or biochemistry, i.e., sensing chemistry or biochemistry is not just coated on arm 24 of FIG. 1A but the entire arm 25 is made of sensing chemistry or biochemistry itself or of the sensing chemistry or biochemistry distributed in a matrix. This is particularly advantageous in an absorption type or fluorescence type sensor, since the light will pass through considerably more sensing chemistry or biochemistry than if a surface coating is used. In the case of absorption, the effective path length is increased, and in the case of fluorescence more of the fluorescing wavelength is trapped in the waveguide, thereby giving greater change in the signal. The sloped reflective end face 32 of FIG. 1A is replaced by reflective element 33 (e.g. a prism) to reflect light passing through arm 25 into detector 18.

Figure 2A:
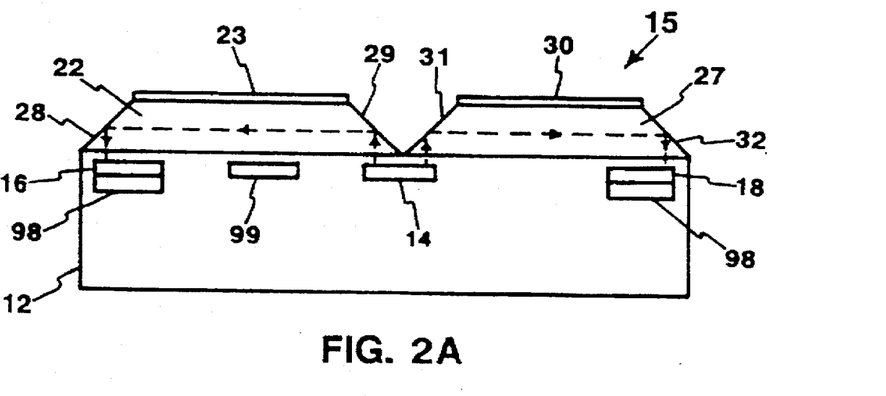
FIGS. 2A,B are side and perspective views of an alternate embodiment of a waveguide sensor having a reference arm and sensing arm.
Figure 2B:
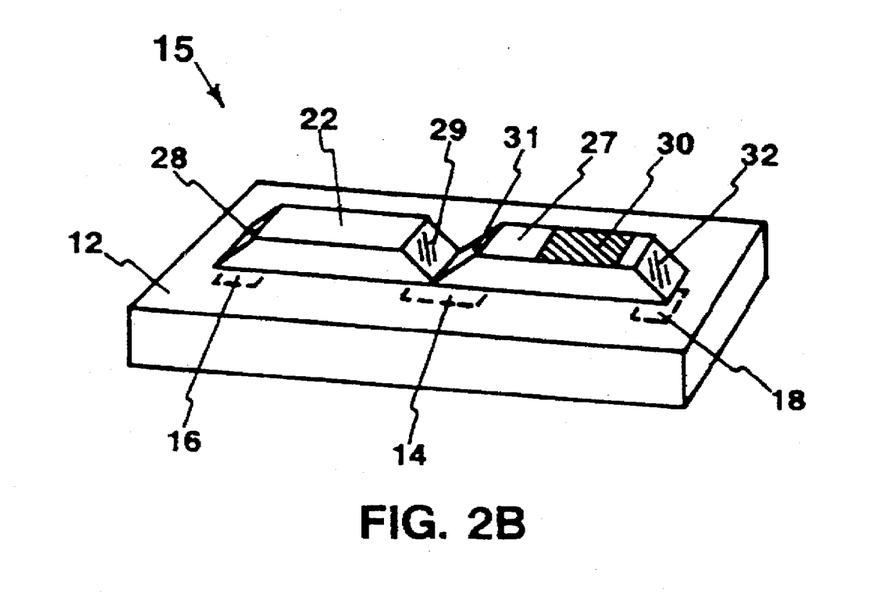

FIGS. 2A,B show a waveguide sensor 15 which is a variation of the sensor 10 of FIGS. 1A,B. In sensor 15, the position of the light source 14 and reference detector 16 are reversed, i.e., the arrangement is still linear but the source 14 is in the center instead of at the end. Reference arm 22 has a sloped reflective end face 29 positioned over source 14 for inputting a portion of the light into arm 22. The light passes along arm 22 to sloped reflective end face 28 which reflects the light down to reference detector 16. Sensing arm 24 of FIGS. 1A,B is replaced by sensing arm 27 which has sensing region 30 formed on a portion thereof. Sensing region 30 can again be a sensing chemistry or biochemistry coated on sensing arm 27 or can be a completely uncoated region on sensing arm 27. Sensing arm 27 has a sloped reflective end face 31 over source 14 which inputs a portion of the light from source 14 into sensing arm 27. After the light interacts with sensing region 30, it is reflected by sloped reflective end face 32 down into detector 18.

Figure 2C:
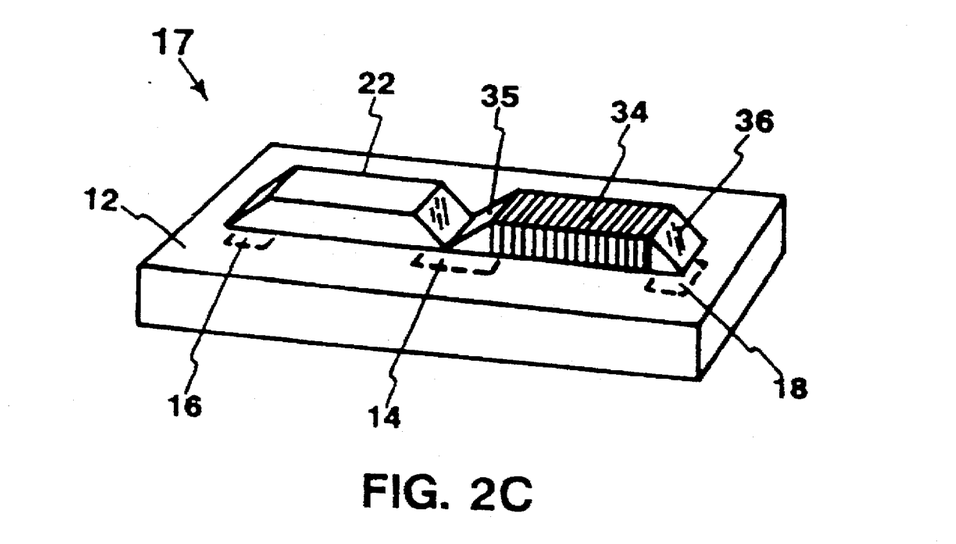
FIG. 2C is a perspective view of the waveguide sensor of FIGS. 2A,B wherein the sensing arm waveguide is formed of the sensing chemistry.

FIG. 2C shows a waveguide sensor 17 which is similar to sensor 15 of FIGS. 2A,B except that sensing arm 27 is replaced with a sensing arm 34 which is formed of the sensing chemistry or biochemistry, or wherein the sensing chemistry or biochemistry is dispersed in an inert matrix. The sloped reflective end faces 31,32 of FIGS. 1A,B are replaced by reflective elements 35,36 (e.g., prisms) that reflect light into and out of arm 34.

Figure 3A:
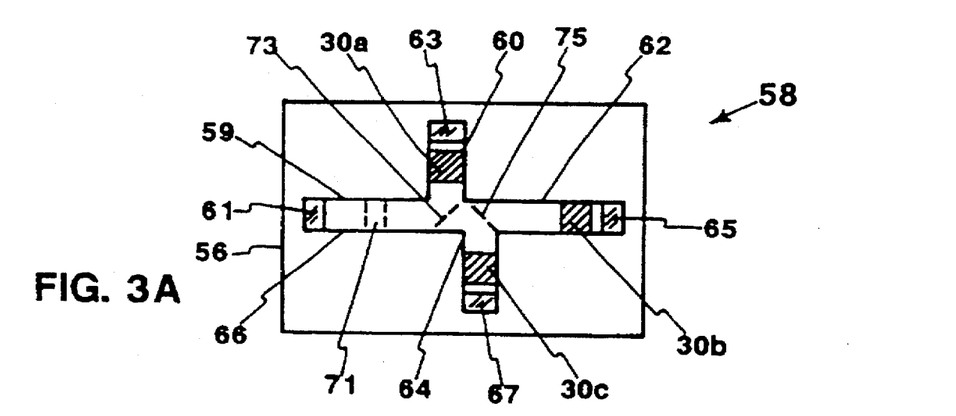
FIGS. 3A-C show a multiple arm waveguide sensor configuration.
Figure 3B:
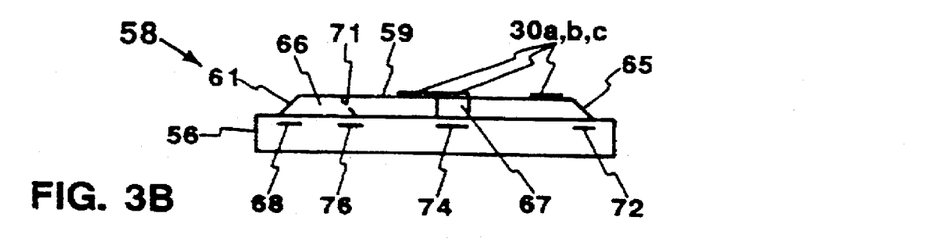
Figure 3C:
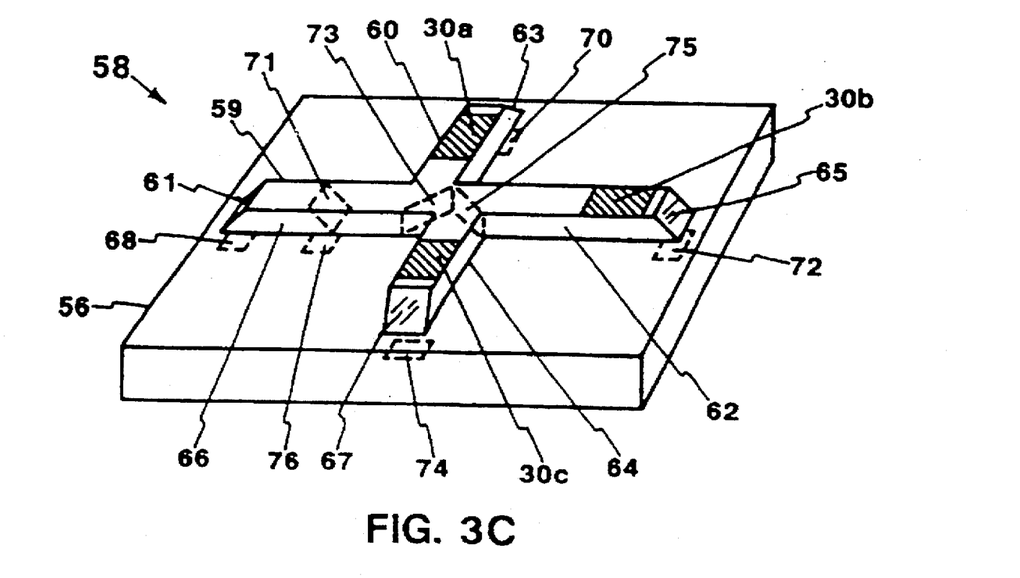

FIGS. 3A–C show a sensor 58 with multiple waveguides on a chip 56. In the arrangement shown, three different waveguides (sensing arms) 60,62,64 are used with single reference arm. This permits three different chemistries or biochemistries 30a,b,c to be used at once and also provides for a reference channel 66. Any of the chemistries 30a,b,c can be replaced with bare sensing regions. The system uses a single light source 68 and multiple detectors 70,72,74. A fourth detector 76 can be used to look at the reference channel 66. Light from source 68 in chip 56 is incident on sloped reflective end face 61 of waveguide 59 which reflects the light down the waveguide 59 to beam splitter 71. Beam splitter 71 reflects a portion of the light to reference detector 76. Beam splitters 73,75 divide the transmitted light into the three sensing waveguides 60,62,64 with sensing regions 30a,b,c respectively, which can be coated with sensing chemistries or biochemistries or contain uncoated regions. The light passing through waveguides 60,62,64, which is affected by sensing regions 30a,b,c, then is reflected by sloped reflective end faces 63,65,67 into detectors 70,72,74, respectively. This arrangement can be used in three approaches: (1) Three different analytes can be analyzed simultaneously or (2) If there is a question of specificity, then coincident or redundant analyses can be accomplished using two or more sensing chemistries or biochemistries which respond to the target analyte or (3) If there is a need for additional sensitivity the same chemistry or biochemistry or lack of coating can be used on all the sensing waveguides and their output signals added. The number of waveguides that can be used is only restricted by source strength and geometric considerations.

Figure 3D:
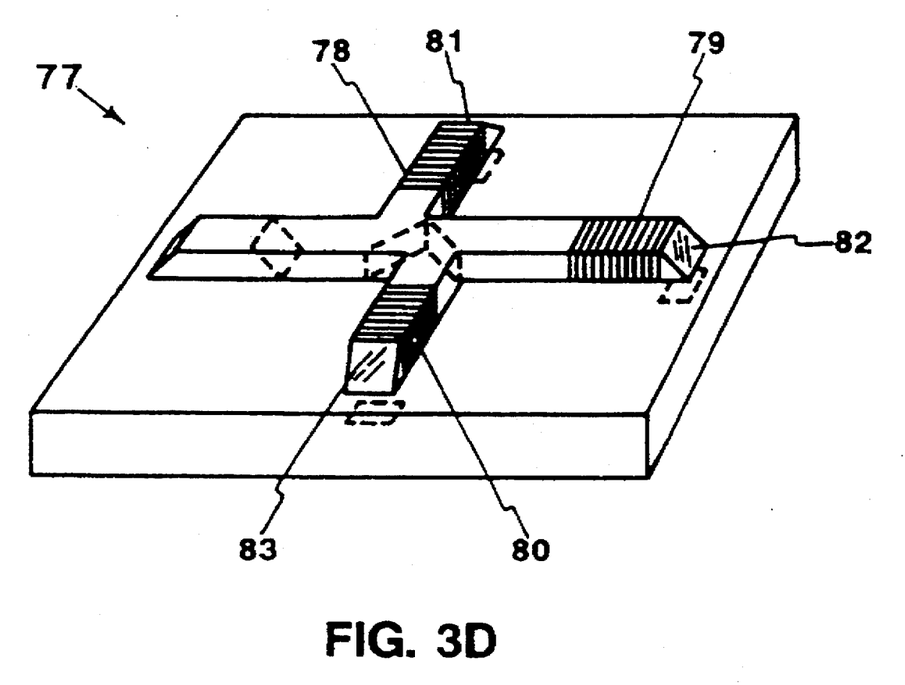
FIG. 3D shows an alternate embodiment of the waveguide sensor of FIGS. 3A-C wherein the sensing arms are formed of sensing chemistries.

FIG. 3D shows a multiple waveguide sensor 77 which is similar to sensor 58 of FIGS. 3A–C except that sensing arms 60,62,64 are replaced by sensing arms 78,79,80 which are formed of the sensing chemistry or biochemistry, or the sensing chemistry or biochemistry homogeneously dispersed in an inert matrix and sloped reflective end faces 63,65,67 are replaced by reflective elements 81,82,83 (e.g., prisms).

Figure 3E:
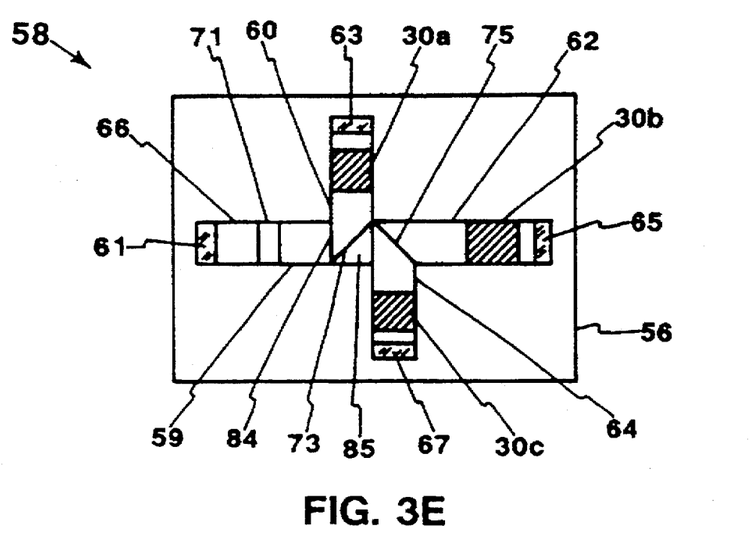
FIG. 3E is a top view of the waveguide sensor of FIGS. 3A-C showing the assembly of the waveguide arms.

FIG. 3E illustrates the construction of the multi-arm waveguide sensor 58 of FIGS. 3A–C. Waveguide 59 with reference channel 66 has a flat end face 84 distal from sloped end 61. Waveguide 60 is placed at right angles to waveguide 59 abutting end face 84. The end of waveguide 60 distal from sloped end 63 is sloped to form beam splitter 73. A matching prism 85 is placed against the sloped end of waveguide 60 (beam splitter 73) to form a flat face against which waveguide 64 is placed as right angles. The end of waveguide 64 distal from sloped end 67 is sloped to form beam splitter 75. Waveguide 62 has a sloped end face, at the end distal from sloped end 65, which matches the sloped end (beam splitter 75) of waveguide 64, so that waveguide 62 is aligned with waveguide 59. Beam splitters 73,75 are formed by applying suitable optical coatings to the ends of waveguides 60,62,64 to produce the desired reflection and transmission characteristics.

Figure 3F:
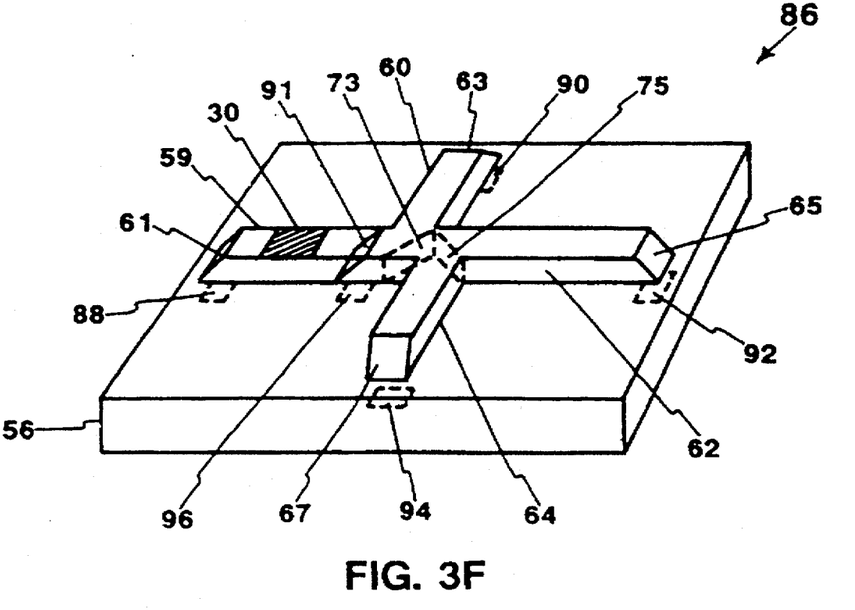
FIG. 3F shows a multiple arm waveguide sensor with multiple sources.

FIG. 3F illustrates a waveguide sensor 86 formed on a substrate or chip 56 which is similar to sensor 58 of FIGS. 3A–C but which has multiple sources and a single detector. Detectors 70,72,74 of sensor 56 are replaced by three sources 90,92,94, typically at three different wavelengths compatible with the sensing chemistry, biochemistry or lack of coating, and source 68 is replaced by a detector 88 which is sufficiently broadband to detect light from all three sources 90,92,94. Beam splitter 73 is highly reflective to the wavelength of source 90 and highly transmissive to the wavelengths from sources 92,94. Beam splitter 75 is highly reflective to the wavelength of source 94 and highly transmissive to the wavelength of source 92. The beam splitter characteristics are obtained by suitable optical coatings. Sloped end faces 63, 65,67 direct light from sources 90,92, 94 down waveguides 60,62,64 and beam splitters 73,75 direct the light beams into waveguide (sensing and reference arm) 59. Waveguide 59 includes beam splitter 91 which directs a portion of the light to reference detector 96. The rest of the light beam passes through waveguide 59 which is coated with (or contains) sensing chemistry or biochemistry or is uncoated to form a sensing region 30. The modulated beam is then reflected by end face 61 down to detector 88. Thus, in this configuration, there is only one sensing region but three different light sources. Waveguides 60,62,64 do not contain any sensing chemistry or uncoated sensing region.

Figure 3G:
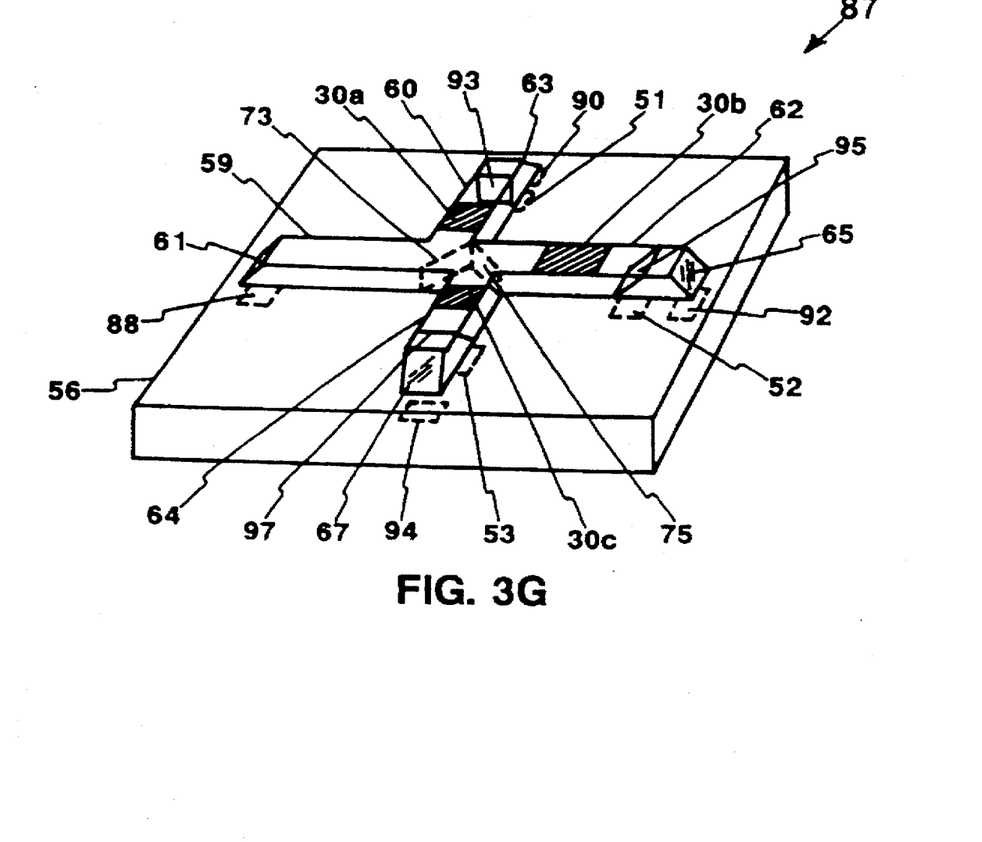
FIGS. 3G,H show an alternate embodiment of a multiple arm waveguide sensor with multiple sources.
Figure 3H:
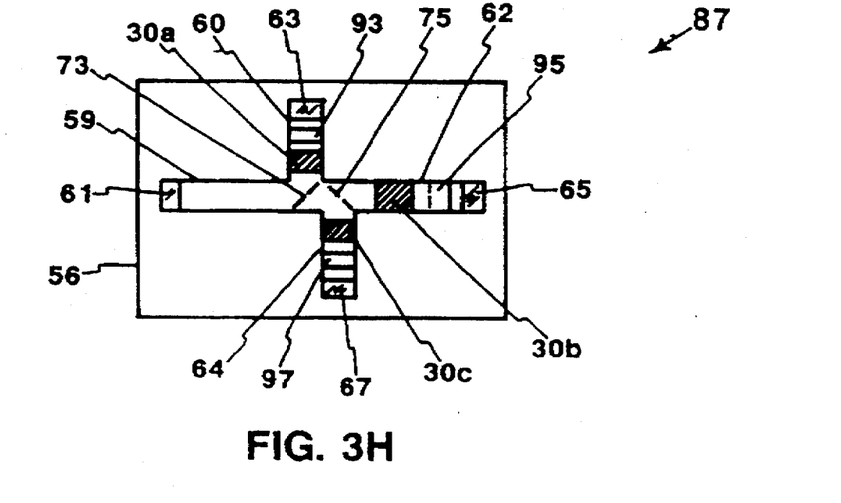

FIGS. 3G,H show an alternate embodiment of sensor 86 of FIG. 3F which has multiple sources and multiple sensing chemistries, biochemistries or uncoated sensing regions. Waveguide sensor 87 on chip 56 has three sources 90,92,94, typically at three wavelengths, and a detector 88. Sloped end faces 63,65,67 direct light from sources 90,92,94 into waveguides 60,62,64 where the light first encounters a beam splitter 93,95,97 which directs a portion of the light down to reference detectors 51,52,53. The remainder of the light passes down waveguides 60,62,64 which are coated with (or contain) sensing chemistry or biochemistry or are uncoated to form sensing regions 30a,b,c. Beam splitters 73,75 pass or direct the modulated light beams from waveguides 60,62,64 to waveguide 59, where the light is reflected at end face 61 down to detector 88. Thus, in this configuration, there is a sensing chemistry or biochemistry or uncoated sensing region on each arm with a source, but there is also a reference detector on each sensing arm. In other combinations the sensing arm can be uncoated and the reference arm can be uncoated, but not at the same time. Permissible combinations are coated sensing arm and coated reference arm, coated sensing arm and uncoated reference arm or uncoated sensing arm and coated reference arm.

Although waveguide sensors can be formed as described above by mounting waveguide structures on a molded chip package which contains the source(s) and detector(s), it is also possible according to the invention to further integrate the waveguide structures into the molded chip package. The waveguide structures of FIGS. 1A–3H can be molded as part of the substrate or chip package 12 or 56. It is also possible to form parts of the waveguide structures, as illustrated in FIGS. 4A–H. In these embodiments, the elements defining the direction of light propagation are formed with the chip as part of the chip fabrication process. Only very simple elements need then be inserted to form a working sensor and these elements are easily interchanged to produce a wide variety of sensors. The design even provides for liquid waveguides, enabling the use of liquid sensing chemistries or biochemistries.

Figure 4A:
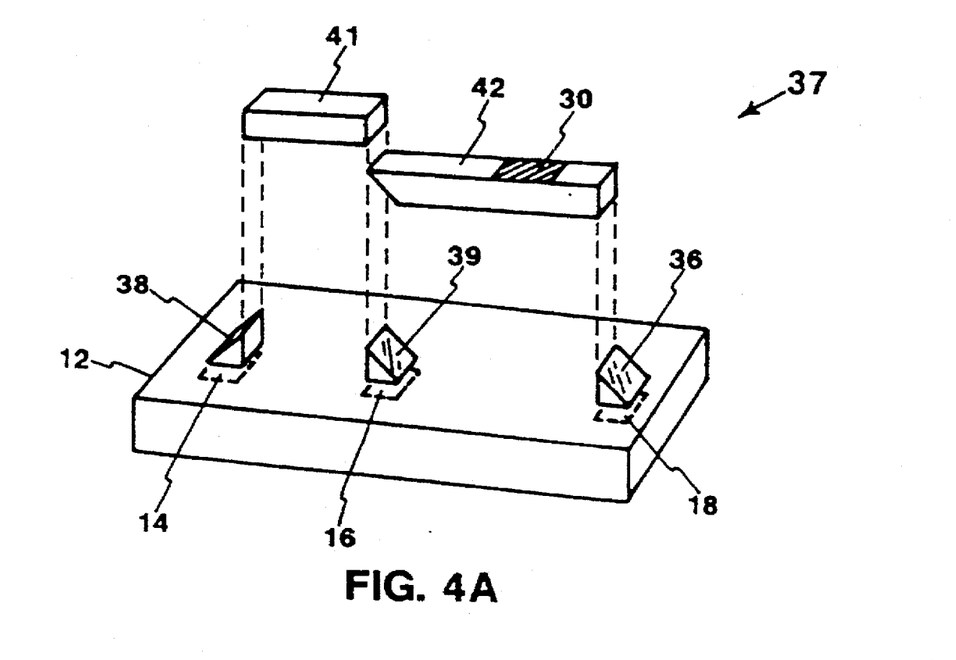
FIGS. 4A-D show of a molded chip package with integral waveguide forming elements.
Figure 4B:
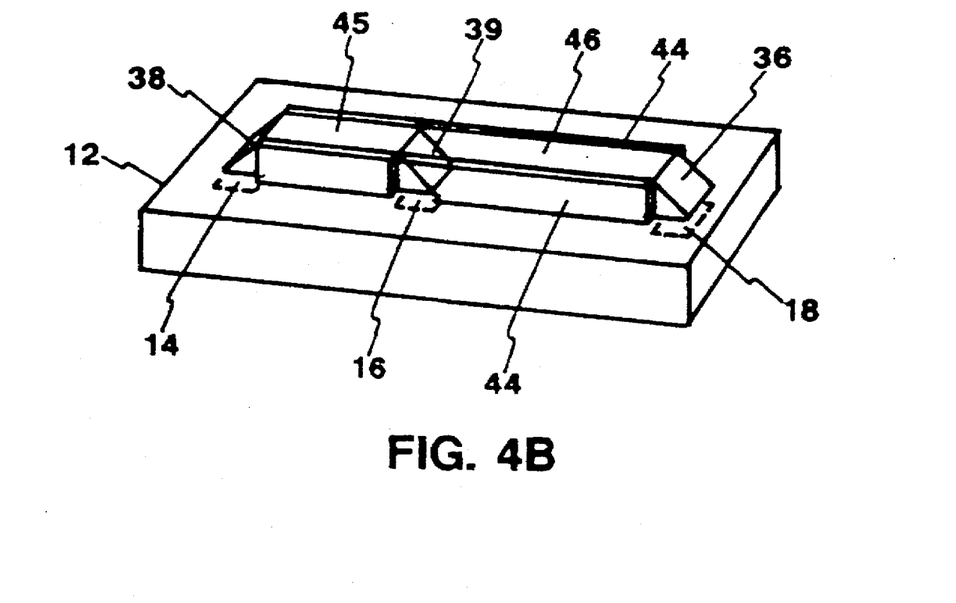
Figure 4C:
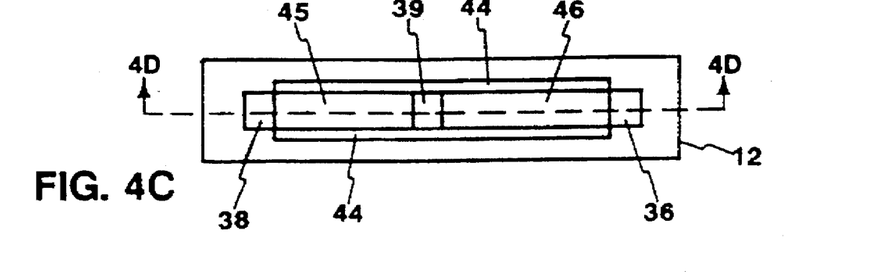
Figure 4D:
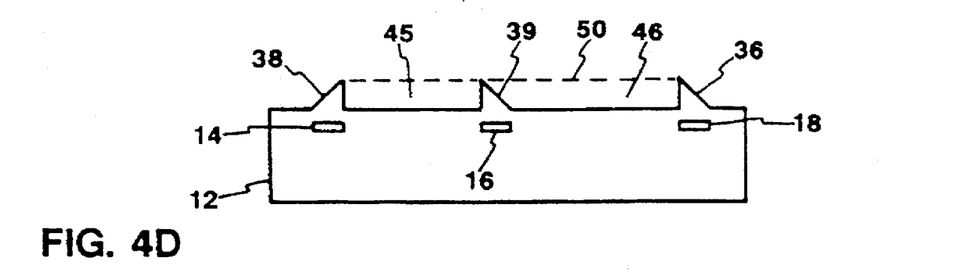

As shown in FIG. 4A, chip 12 with source 14 and detectors 16,18, is formed with waveguide defining elements 36,38,39 formed integrally thereon, i.e., when chip 12 is molded, elements 36,38,39 are formed as part of the molding process. Elements 38,39,36 are formed over source 14 and detectors 16,18, respectively. Source 14 is at one end of the linear arrangement. Elements 36,38 are corner reflectors and element 39 is a beam splitter. A waveguide body 41 can be easily inserted between elements 38,39 and a waveguide body 42, which can be coated with sensing chemistry or biochemistry or uncoated to form a sensing region 30 (or alternatively is partly formed of the sensing chemistry) can be easily inserted between elements 39,36 to form a waveguide sensor 37. As shown in FIG. 4B, the spaces between elements 36,38,39 can be enclosed by lateral walls 44, defining channels 45,46. FIGS. 4C,D are top and side sectional views. Inserts 41,42 of FIG. 4A can be inserted in channels 45,46 or channels 45,46 can be filled with liquid reagents and then covered with a membrane 50, as shown in FIG. 4D. Membrane 50 can be attached to side walls 44. Channels 45,46 can also be filled with liquid or solid reagents dispersed in a sol-gel or porous glass or other absorbing materials which are optically transparent and allowed to coagulate, thus obviating the need for a membrane except in situations where the membrane provides additional specificity or physical protection of the sensing chemistry or biochemistry. Channels 45,46 can also be filled with multiple layers of sol-gel or other absorbing material having different reagents dispersed therein.

Figure 4E:
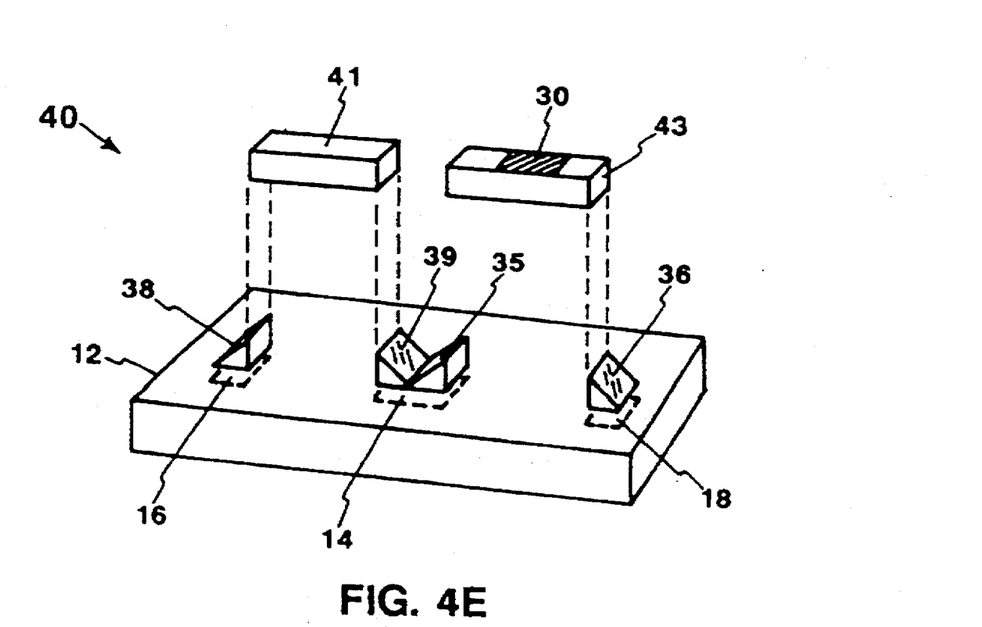
FIGS. 4E-H show an alternate embodiment of a molded chip package with integral waveguide forming elements.
Figure 4F:
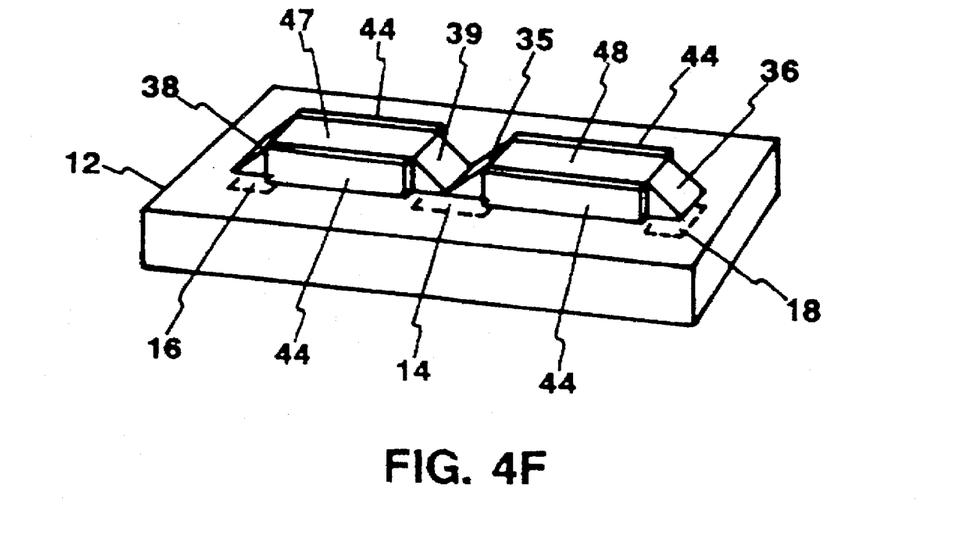
Figure 4G:
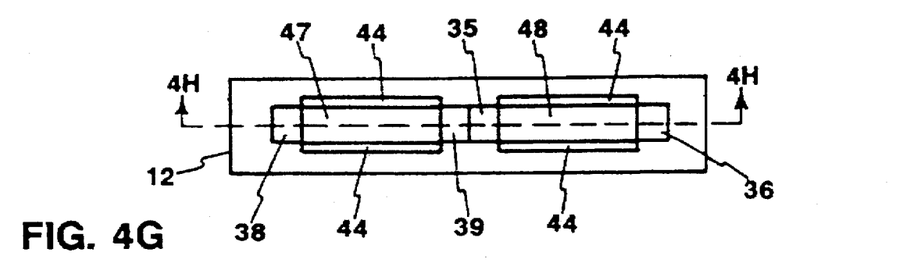
Figure 4H:
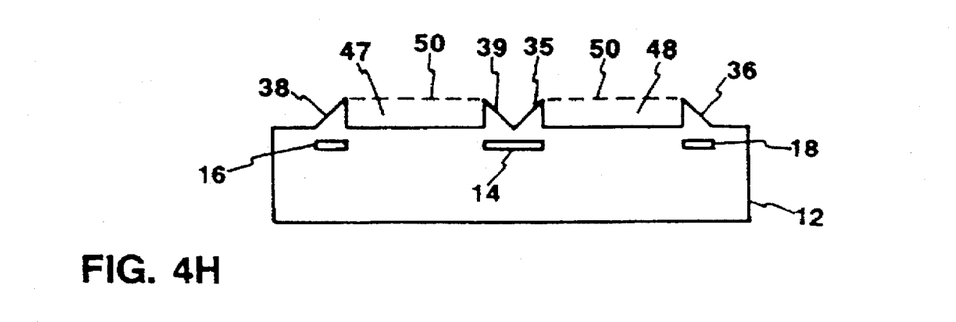

FIG. 4E shows an alternate embodiment of a chip 12 with integral waveguide defining elements 35,36,38,39. In this case, source 14 is in the center with detectors 16,18 at the ends. Again, elements 35,36,38,39, which are corner reflectors, are formed as part of the fabrication process of chip 12. A waveguide body 41 can be easily inserted between elements 38,39 and a waveguide body 43 which is coated with (or contains) a sensing chemistry or biochemistry or is uncoated to form a sensing region 30, can be easily inserted between elements 35,36 to form a waveguide sensor 40. As shown in FIG. 4F, the spaces between elements 35,36,38,39 can be enclosed by lateral walls 44, defining channels 47,48. FIGS. 4G–H are top and side sectional views. Inserts 41,43 of FIG. 4E can be inserted in channels 47,48 or channels 47,48 can be filled with liquid reagents and then covered with a membrane 50, as shown in FIG. 4H. Membrane 50 can be attached to side walls 44. Channels 47,48 can also be filled with one or more layers of liquid or solid reagents dispersed in a sol-gel or porous glass or other absorbing materials and allowed to coagulate, thus obviating the need for a membrane except in situations where the membrane provides additional specificity or physical protection of the sensing chemistry or biochemistry.

The molded integrated chip package 12 which contains the source 14 and detectors 16,18 can also include other electronics, as shown in FIGS. 1A,2A. Associated with each detector 16,18 can be an amplifier 98 or other signal processing electronics. A feedback circuit 99 can also be included, connected between source 14 and reference detector 16 to maintain a constant source output.

Changes and modifications in the specifically described embodiments can be carried out without departing from the scope of the invention which is intended to be limited only by the scope of the appended claims.

We claim:

1. An optical sensor comprising:

a modular substrate having at least one light source and at least one light detector formed internally therein and covered by an optically transparent material;

a waveguide structure mounted on said substrate and extending over said at least one source and at least one detector, said waveguide structure including direction turning means for guiding light from said at least one source into said waveguide structure and direction turning means for guiding light from said waveguide structure to said at least one detector;

a sensing region formed on or in a portion of the waveguide structure, wherein the sensing region is a sensing chemistry selected from the group consisting of inorganics, organics, polymers, metals, metal compounds, and organometallics; a sensing biochemistry selected from the group consisting of antibodies, enzymes, microbes and bioinorganics; or an uncoated portion of the waveguide which acts as a sensing element.

2. The sensor of claim 1 wherein the modular substrate has one source and first and second detectors in a linear arrangement with the source at one end, and the waveguide structure is formed of a first waveguide body which extends from said source to the first detector and a second waveguide body forming a junction with the first waveguide body and extending between the first and second detectors.

3. The sensor of claim 2 wherein the direction turning means for guiding light from the source into the waveguide structure comprises a sloped reflective end face formed on the first waveguide body, and the direction turning means for guiding light from the waveguide structure to the first and second detectors comprises a beam splitter formed at the junction between the first and second waveguide bodies and a sloped reflective end face formed at the distal end of the second waveguide body.

4. The sensor of claim 3 wherein the sensing region is formed on or in the second waveguide body and the first detector forms a reference detector.

5. The sensor of claim 1 wherein the modular substrate has one source and two detectors in a linear arrangement with the source located between the two detectors, and the waveguide structure is formed of a first waveguide body which extends from said source to one detector and an adjacent second waveguide body which extends from said source to the other detector.

6. The sensor of claim 5 wherein the direction turning means for guiding light from the source into the waveguide structure comprises a sloped reflective end face formed on one end of each waveguide body and the direction turning means for guiding light from the waveguide structure to the detectors comprises a sloped reflective end face formed on an end of each waveguide body distal from said one end.

7. The sensor of claim 6 wherein the sensing region is formed on or in one waveguide body and the other waveguide body forms a reference arm.

8. The sensor of claim 1 wherein the modular substrate has one source and a plurality of detectors in a geometric pattern, and the waveguide structure comprises a plurality of interconnected arms extending from the detectors to the source.

9. The sensor of claim 8 wherein a sensing region is formed on or in each arm which extends to a detector.

10. The sensor of claim 9 wherein each arm which extends to a detector has a different sensing region formed thereon or therein.

11. The sensor of claim 8 wherein the modular substrate has one source and three detectors and the waveguide structure comprises a first waveguide arm extending from the source and three sensing arms extending from the first waveguide arm to a respective detector, one sensing arm being aligned with the first waveguide arm and two being orthogonal, and further comprising a pair of beam splitters formed in the sensing arms for splitting light from the source among the three sensing arms.

12. The sensor of claim 11 further comprising a beam splitter in the first waveguide arm and a reference detector below the beam splitter.

13. The sensor of claim 1 wherein the modular substrate has one detector and a plurality of sources in a geometric pattern, and the waveguide structure comprises a plurality of interconnected arms extending from the sources to the detector.

14. The sensor of claim 13 wherein the sensing region is formed on or in an arm of the waveguide structure near the detector, and further comprising a beam splitter between the waveguide arms from the detectors and the sensing region and a reference detector below the beam splitter.

15. The sensor of claim 13 wherein a sensing region is formed on or in each arm which extends to a source, and further comprising a beam splitter in each said arm between the source and sensing region and a reference detector below each beam splitter.

16. The sensor of claim 1 wherein the modular substrate is a semiconductor chip package.

17. The sensor of claim 1 further comprising removable waveguide body inserts which fit between said direction turning means.

18. The sensor of claim 17 wherein the sensing region is formed on or in a waveguide body insert.

19. The sensor of claim 1 further comprising lateral walls defining open channels between said direction turning means.

20. The sensor of claim 19 further comprising a liquid reagent filling said open channels and a membrane covering said liquid reagent filled channels.

21. The sensor of claim 19 further comprising a liquid or solid reagent dispersed in a sol-gel or porous glass or other absorbing materials which are optically transparent and allowed to coagulate filling said open channels.

22. The sensor of claim 21 further comprising a plurality of layers of sol-gel or porous glass or other absorbing materials which are optically transparent and allowed to coagulate having different reagents dispersed therein.

* * * * *